(12) United States Patent
Mitterer et al.

(10) Patent No.: US 6,831,159 B1
(45) Date of Patent: Dec. 14, 2004

(54) METHOD FOR PURIFYING FACTOR VIII/ VWF COMPANY BY CATION-EXCHANGE CHROMATOGRAPHY

(75) Inventors: Artur Mitterer, Mannsdorf (AT); Bernhard Fischer, Vienna (AT); Öyvind L. Schönberger, Vienna (AT); Kathrin Thomas-Urban, Freiburg (DE); Friedrich Dorner, Vienna (DE); Johann Eibl, Vienna (AT)

(73) Assignee: Baxter Aktiengesellschaft, Vienna (AU)

( * ) Notice: Subject to any disclaimer, the term of this patent is extended or adjusted under 35 U.S.C. 154(b) by 0 days.

(21) Appl. No.: 09/367,459

(22) PCT Filed: Feb. 27, 1998

(86) PCT No.: PCT/AT98/00043

§ 371 (c)(1),
(2), (4) Date: May 8, 2000

(87) PCT Pub. No.: WO98/38220

PCT Pub. Date: Sep. 3, 1998

(30) Foreign Application Priority Data

Feb. 27, 1997 (AT) ................................................ 338/97

(51) Int. Cl.[7] ................................................. A23J 1/00
(52) U.S. Cl. ........................ 530/412; 530/412; 530/350; 435/7.1; 514/21
(58) Field of Search .......................... 435/7.1; 530/412, 530/350; 514/21

(56) References Cited

U.S. PATENT DOCUMENTS

| | | | | |
|---|---|---|---|---|
| 4,578,218 A | * | 3/1986 | Saundry et al. ............. | 530/383 |
| 5,679,776 A | * | 10/1997 | Burnouf-Radosevich et al. | 530/383 |
| 5,789,153 A | * | 8/1998 | Falkner et al. .................. | 435/5 |
| 5,858,658 A | * | 1/1999 | Haemmerle et al. ........... | 435/6 |
| 5,876,969 A | | 3/1999 | Fleer et al. ................. | 435/69.7 |
| 5,877,152 A | | 3/1999 | Fischer et al. ................. | 514/12 |
| 5,880,265 A | | 3/1999 | Fischer et al. .............. | 530/383 |
| 6,103,693 A | | 8/2000 | Fischer et al. ................. | 514/12 |
| 6,228,613 B1 | | 5/2001 | Fischer et al. ............. | 435/69.1 |

FOREIGN PATENT DOCUMENTS

| | | |
|---|---|---|
| AU | 737986 | 9/1998 |
| CA | 2251558 | 10/1998 |
| EP | 0 131 740 B1 | 10/1985 |
| EP | 0 295 645 A2 | 12/1988 |
| EP | 0 600 480 A2 * | 6/1994 |
| WO | WO 91/13093 | 9/1991 |
| WO | WO 93/15199 | 8/1993 |
| WO | WO 97/39033 | 8/1993 |
| WO | WO 96/10584 | 4/1996 |
| WO | WO 97/34930 | 9/1997 |
| WO | WO 98/38219 | 9/1998 |

OTHER PUBLICATIONS

International Search Report for PCT/AT 98/00043.
International Search Report for PCT/AT 99/00048.
International Search Reprot for PCT/AT98/00043, dated Jul. 3, 1998.
International Search Report for PCT/AT99/00048, dated Jun. 9, 1999.
Berntorp, E., "Plasma Product Treatment in Various Types of von Willebrand's Disease", *Haemostasis*, vol. 24, 1994, pp. 289–297.
Bourgois, A. et al., "Blood–coagulation Factor (vWF) Complex", *Chem. Abs.*, vol. 105, 1986, p. 380, Abstract No. 178421n.
Harrison, R.H., et al., "Chromatography of the VIII/vWF Complex on Dextran Sulphate Sepharose", *Thromb. Res.*, vol. 50, 1988, pp. 295–304.
Harrison, P. et al., "The Purification of the VIII/vWF Complex Using Dextran Sulfate Sepharose Chromatography", *Chem. Abs.*, vol. 112, 1990, p. 274, Abstract No. 11822b.
Koops, et al., "Immunoaffinity Purification of Factor VIII/ von Willebrand Factor Complex", *Chem. Abs.*, vol. 117, 1992, p. 324, Abstract No. 3089f.
Lethagen, et al., "Pharmacokinetics and Hemostatic Effect of Different Factor VIII/von Willebrand Factor Concentrates in von Willebrand's Disease Type III", *Ann. Hematol.*, vol. 65, 1992, pp. 253–259.
Mejan, O. et al., "Immunopurification of Human Factor VIII/vWF Complex From Plasma", *Pharmaceuticals*, vol. 109, 1988, p. 357, Abstract No. 115910h.
Ruttyn, Y. et al., "Chromatography of Human Plasma on Aminohexyl Sepharose: Separation of Factor VIII/vWF and Behavior of Factors II, VII, IX and X and Antithrombin III", *Enzymes*, vol. 111, 1989, p. 311, Abstract No. 149359s.
Saundry et al., "The Interaction of the Factor VIII/von Willebrand Factor Complex with Immobilized Metal Affinity Chromatogrphy (IMAC) Matrixes", *Biochem. Methods*, vol. 112, 1990, p. 252, Abstract No. 18400w.
English translation of Official Action for A338/97, dated Sep. 1, 1997 (1st Preliminary Notice).
English translation of Official Action for A 866/98 dated May 20, 1998 (1st Preliminary Notice).
English translation of Official Action for A 866/98 dated May 20, 1996 (2nd Preliminary Notice).

* cited by examiner

Primary Examiner—Christopher S. F. Low
Assistant Examiner—Hope A. Robinson
(74) Attorney, Agent, or Firm—Townsend and Townsend and Crew LLP

(57) ABSTRACT

Methods for recovering factor VIII/vWF-complex that involve binding factor VIII/vWF-complex from a protein solution to a cation exchanger and recovering factor VIII/ vWF-complex by step-wise elution are disclosed. The recovered complex contains high-molecular vWF multimers. Compositions containing factor VIII/vWF-complex as purified by cation exchange chromatography are also provided.

11 Claims, 2 Drawing Sheets

METHOD FOR PURIFYING FACTOR VIII/VWF COMPANY BY CATION-EXCHANGE CHROMATOGRAPHY

CROSS-REFERENCES TO RELATED APPLICATION

This application is the U.S. national phase of PCT/AT98/00043, filed Feb. 27, 1998, which claims priority to Austrian Application A 338/97, filed Feb. 27, 1997.

FIELD OF THE INVENTION

The invention relates to a method of purifying factor VIII/vWF-complex from a biological starting material by means of cation exchange chromatography and step-wise elution, as well as purified factor VIII/vWF-COMPLEX complex which particularly comprises high-molecular vWF multimers.

BACKGROUND von Willebrand factor circulates in plasma at a concentration of from 5 to 10 mg/l, mainly in the form of a non-covalently bound complex with factor VIII. In the cryoprecipitate, factor VIII/vWF-complex is highly enriched and can be isolated therefrom or from plasma or from plasma fractions by means of known fractionation methods.

In hemophilia, blood coagulation is impaired by a deficiency of certain plasmatic blood coagulation factors. In hemophilia A, the bleeding inclination is based on a deficiency of factor VIII or of vWF, respectively (phenotypic hemophilia). Treatment of hemophilia A is mainly effected by substituting the missing coagulation factor by factor concentrates, e.g. by infusion of factor VIII or of factor VIII/vWF-complex.

A purified factor VIII, complexed with vWF, is desirable for utilization in the therapy of patients suffering from hemophilia A, but also for von Willebrand syndrome (Berntorp, 1994, Haemostasis 24:289–297). In particular, it has been emphasized repeatedly that in preparations lacking vWF or having only a low content thereof, an increased bleeding time and a low factor VIII:C half-life can be observed in vivo. Normalization of vWF in vivo is important so as to maintain a concentration of factor VIII in plasma both by reducing the factor VIII elimination rate and by aiding the release of endogenous factor VIII (Lethagen et al., 1992, Ann. Hematol. 65: 253–259).

DE 3 504 385 describes the execution of an ion exchange chromatography for the purification of factor VIII/vWF-complex, wherein the factor VIII complex is bound via sulfate groups and is eluted with citrated buffer, calcium chloride and NaCl gradient. Therein, the factor VIII/vWF-complex is eluted from the carrier at a concentration of 0.5 M NaCl.

EP 0 416 983 describes the recovery of the factor VIII/vWF-complex from human plasma by a combination of barium chloride- or aluminum hydroxide-precipitation and anion exchange chromatography on DEAE Fractogel.

Harrison et al. (Thrombosis Res., 1988; 50, 295–304) describes the purification of factor VIII/vWF-complex by chromatography on dextrane-sulphate-sepharose.

EP 0 600 480 describes a purification method for factor VIII/vWF-complex from whole plasma by means of combined anion exchange/cation exchange chromatography. The elution of the FVIII/vWF-complex adsorbed on the cation exchanger there is effected by using a Ca-containing buffer having 0.3 M NaCl in a pH range of between 6.6 and 7.0.

WO 96/10584 describes a method of recovering highly-purified recombinant vWF by means of a combined anion exchange/heparin affinity chromatography, and EP 0 705 846 describes the separation between high and low molecular fractions of recombinant vWF by means of heparin affinity chromatography.

The factor VIII preparations described in the prior art to the greatest part do contain the entire vWF multimer pattern, yet they vary as regards their portions of high-molecular vWF (HMW-vWF) and low-molecular vWF (LMW-vWF), and they also exhibit so-called triplet structures suggesting a proteolytic degradation, in particular of HMW-VWF. The stability of these preparations often is limited thereby.

It has been emphasized repeatedly that factor VIII/vWF preparations containing substantially HMW-vWF possibly might have a positive influence on the bleeding time, since they carry out the primary function of vWF, the platelet agglutination, and have a higher affinity to the platelet receptors glycoprotein IB and IIb/IIIa than low-molecular vWF multimers.

There has been a demand for a factor VIII complex having a sufficiently specific activity of factor VIII:C- and vWF-activity. One problem in the recovery of such a complex particularly is the separation of molecules containing low-molecular vWF multimers, and the enrichment of complexes with a high specific vWF activity.

SUMMARY

Thus, it is the object of the present invention to provide a factor VIII/vWF complex having improved specific activity and stability.

It is a further object to provide a method of recovering such a factor VIII/vWF-complex. The method should be usable for the purification of both, a recombinant and a plasmatic factor VIII/vWF complex.

According to the invention, this object is achieved in that a method of recovering factor VIII/vWF-complex is provided, in which factor VIII/vWF-complex from a protein solution is bound to a cation exchanger, and factor VIII/vWF-complex having an improved specific vWF activity is recovered by step-wise fractionated elution. The recovery and enrichment of factor VIII/vWF having improved activity and stability is particularly effected in that factor VIII/vWF complex is bound at a low salt concentration, that by a step-wise raising of the salt concentration, fractions containing factor VIII/vWF-complex with low-molecular vWF multimers, inactive vWF degradation products and unspecific accompanying proteins are separated at a medium salt concentration, and fractions containing factor VIII/vWF-complex that particularly contains high-molecular vWF multimers are recovered at a higher salt concentration.

On account of its acidic isoelectric point (IEP=5.5 to 6) and its negative net charge resulting therefrom, factor VIII/vWF-complex usually is purified in a weakly acidic to basic environment via positively charged anion exchangers. Thus, on account of the methods described so far of purifying factor VIII/vWF-complex by means of positively charged anion exchangers, it could not be expected for factor VIII/vWF -complex to bind also to a negatively charged gel matrix of a cation exchanger at a pH lying above the IEP of the complex and at a low salt concentration, and to be selectively elutable therefrom by raising the salt concentration. Neither could it be expected that by a step-wise elution at a salt concentration of approximately between $\geq 250$ mM and $\leq 300$ mM, unspecific accompanying proteins, inactive vWF degradation products, complex components having a low specific activity, factor VIII/vWF-complex containing low-molecular vWF multimers, non-complexed or merely weakly bound factor VIII and free factor VIII are eluted, and that at a salt concentration of ≧300 mM in particular factor VIII/vWF-complex with high-molecular vWF multimers is obtained.

It has been found within the scope of the present invention that with the method according to the invention, departing from an impure biological material, purified fractions are obtained which are substantially free from contaminating nucleic acids. Thereby also nucleic acids are removed from protein preparations by this method. This effect cannot be demonstrated with conventional methods by means of anion exchangers, since nucleic acids, on account of their negative charge, bind to the anion exchanger, detach from the anion exchanger again by increasing the salt concentration, and get into the eluate.

When purifying the factor VIII/vWF complex, particular attention must be paid that, on account of the size of vWF ranging from 500 000 to several millions, only such carrier materials which do not impede the diffusion and distribution of the factor VIII/vWF complex in the carrier materials used will result in good purification and good yields. When carrying out the method according to the invention of purifying factor VIII/vWF-complex with a high specific activity by means of cation exchanger, a gel matrix is used which has not only a high loading capacity, is robust to handle and has a clear elution profile, but which also can be used economically on an industrial scale. Thus, the method according to the invention is particularly interesting for the recovery of purified factor VIII/vWF-complex on a large technical scale.

Every known cation exchanger can be used for carrying out this method, cation exchangers having a sulfopropyl- or carboxymethyl-group conjugated carrier being preferred. SP-Sepharose® Fast Flow and CM-Sepharose® Fast Flow (Pharmacia), Fractogel> EMD-SO3 and Fractogel® EMD COOH (Merck), Poros® 10 SP and Poros® 10 S (Perseptive Biosystems) and Toyopearl™ SP 550 C and Toyopearl™ CM-650 (M) (TosoHaas) have, e.g., proved to be well suitable.

A large-porous gel having tentacle structure of the type of Fractogel® EMD-SO3 and Fractogel® EMD COOH (Merck) has proved particularly suitable for the recovery of purified vWF.

The adsorption of the factor VIII/vWF-complex on the cation exchanger is preferably effected at a salt concentration in the buffer of ≦250 mM. Preferred adsorption buffers thus have a salt concentration of from 50 to 250 mM, in particular in a range of from 150 to 250 mM (e.g. 150 mM). By a step-wise raising of the salt concentration in the buffer, factor VIII/vWF-complex particularly containing high-molecular vWF multimers can be eluted selectively at a salt concentration of ≧300 mM, preferably ≧350 mM. Factor VIII/vWF complex containing low-molecular vWF multimers and proteolytic vWF degradation products which are contained in the protein solution and which have a low specific activity in terms of vWF activity, in particular in terms of Ristocetin-cofactor activity, which have a collagen binding activity and which have a specific platelet agglutination activity, as well as free factor VIII:C are eluted from the cation exchanger at a salt concentration of between ≧250 mM and ≦300 mM, preferably at 300 mM, and optionally are recovered. This fraction may be used for further purification of, e.g., factor VIII:C, which, in particular, is free from platelet-agglutinating vWF activity.

Adsorption and desorption of factor VIII/vWF may be effected in a buffer containing a mono- or bivalent metal ion as salt, NaCl being preferably used as the salt.

In the method according to the invention, as the buffer system for eluting the proteins bound to the cation exchanger, a buffer solution comprised of buffer substances, in particular glycine, phosphate buffer or citrated buffer, and salt are used.

The elution buffer may have a pH ranging between 4.5 and 8.5, preferably between ≧7.0 and ≦8.5.

The method according to the invention may be carried out as a batch method or as a column chromatography.

The optimal parameters, such as salt concentration, pH and temperature for carrying out the method according to the invention are, however, each dependent on the cation exchanger material used. Optimization of the conditions disclosed within the scope of the present invention for carrying out the method for each individually used cation exchanger type is, however, within the general knowledge of a skilled artisan.

In particular, by means of the method according to the invention a factor VIII/vWF-complex is recovered and enriched, which particularly contains high-molecular vWF multimers.

The recovered factor VIII/vWF complex fraction is substantially free from low-molecular vWF multimers, vWF fragments with a low specific activity and contaminating nucleic acids.

Any factor VIII-complex-containing solution may be used as the starting material for recovering purified factor VIII/vWF-complex by means of the method according to the invention. Starting materials are in particular biological materials, such as plasma, a plasma fraction, cryoprecipitate or a supernatant or extract of a recombinant cell culture.

Factor VIII/vWF-complex-containing solutions may, however, also be enriched protein solutions which have been pre-purified or enriched by a preceding step, e.g. via gel filtration, anion exchange chromatography, affinity chromatography or a combination thereof.

According to a particular embodiment of the method of the invention, a factor VIII/vWF-complex containing fraction enriched via an anion exchanger is used as the starting solution. In the subsequent cation exchange chromatography, there occurs a purification and a separation of factor VIII/vWF-complex containing high-molecular and low-molecular vWF-multimers, respectively. Yet also other combinations, such as affinity/cation exchange chromatography, anion exchange/affinity/cation exchange chromatography are possible to attain an enrichment and a selective recovery of factor VIII/vWF having an improved specific activity and stability.

By means of the above-described method according to the invention, factor VIII/vWF having an improved specific activity is manifold enriched from an impure factor VIII/vWF-containing material.

Since, in principle, any biological material may be contaminated with infectious pathogens, the factor VIII/vWF-containing fraction obtained is treated for an inactivation or depletion of viruses so as to produce a virus-safe preparation. To this end, all the methods known from the prior art, such as chemical/physical methods, inactivation by combination of a photoactive substance and light, or depletion by filtration may be used. In particular, a heat treatment in solution or in the solid state, respectively, which reliably can inactivate both lipid-enveloped and non-lipid-enveloped viruses is suitable for an inactivation of viruses. The virus depletion preferably is effected by means of a filtration over nanofilters.

According to a further aspect, the present invention provides purified factor VIII/vWF complex which particularly contains high-molecular vWF multimers, obtainable from a factor VIII/vWF-containing solution by cation exchange chromatography. Factor VIII/vWF having an increased specific vWF activity of preferably at least 66 U/mg protein, and an increased specific factor VIII activity of preferably at least 500 U/mg protein is enriched starting from a starting material containing, i.a., factor VIII/vWF of low purity and low specific activity, and accompanying proteins, in particular factor VIII that is not bound or only weakly bound and thus is free, or factor VIII complex having a low vWF activity, are selectively separated. Thereby, a factor VIII/vWF complex is recovered which contains high-molecular vWF multimers and which substantially is free from factor VIII complex with low-molecular vWF multimers, vWF degradation products, non-complexed factor VIII and, possibly, factor VIIIa. Due to the selective enrichment of high-molecular vWF multimers, the factor VIII/vWF complex according to the invention has an improved platelet agglutination activity and an increased stability.

According to a further aspect, a factor VIII:C which is substantially free from platelet-agglutinating vWF activity, obtainable from a factor VIII/vWF-containing solution, is provided by means of cation exchange chromatography and step-wise elution at a salt concentration of between $\geq 200$ mM and $\leq 300$ mM.

According to a further aspect, a purified preparation containing factor VIII/vWF-complex which particularly contains high-molecular vWF multimers, or factor VIII:C, substantially free from platelet agglutinating vWF activity, is provided.

When recovering and producing the preparation according to the invention with a starting material of plasmatic or recombinant origin, optionally a virus depletion/or inactivation method is carried out, as has been described above, to remove infectious particles, a virus inactivation and/or a virus depletion in principle being possible before or after each purification step, starting from the starting material up to the pharmaceutical preparation produced. Thereby the preparation according to the invention in any event will be virus-safe and free from any infectious material.

A further criterion for the purity and the low infectiousness of a product is also the absence of contaminating nucleic acids. The preparation according to the invention thus is substantially free from nucleic acids. "Substantially" here means that the content of nucleic acids is $\leq 0.7$, based on the ratio 260/280 nm. The nucleic acid may, however, also be quantitated according to a method, e.g., as has been described in EP 0 714 987 and EP 0 714 988.

According to a further aspect, the preparation according to the invention is present in storage-stable form. The preparation containing purified factor VIII/vWF with an improved specific vWF activity may be provided as a ready solution, lyophilisate, or in the deep-frozen state. On account of its purity, the preparation is particularly stable. It has been shown that the preparation according to the invention is stable for at least 6 months at $-20°$ C., in solution for at least 4 weeks at $4°$ C., and as a lyophilisate for at least 1 year. It has been shown that within each respective period of time, the factor VIII/vWF activity is reduced by 10% at the most, and the multimer pattern of the vWF multimers does not show any substantial change.

The formulation of the preparation according to the invention may be effected in a known and common manner. The purified factor VIII/vWF contained in the preparation of the invention, is mixed with a buffer containing salts, such as NaCl, trisodium citrate dihydrate and/or $CaCl_2$, and amino acids, such as glycine and lysine, at a pH ranging from 6 to 8, and formulated into a pharmaceutical preparation.

The preparation may be used for producing a medicament for treating patients suffering from hemophilia, phenotypic hemophilia, and vWD.

According to a further aspect, the present invention relates to a method of preparing a factor VIII/vWF-complex-preparation from plasma or from a plasma fraction, which is characterized in that plasma or a plasma fraction is contacted with a cation exchanger, the factor VIII/vWF-complex being adsorbed thereby, the cation exchanger loaded with factor VIII/vWF-complex optionally is washed, subsequently the factor VIII/vWF-complex is eluted, an eluate being obtained which has an at least 300-fold purity as regards the factor VIII/vWF-complex and a yield of factor VIII/vWF-complex of at least 50%, based on plasma, and subsequently the obtained eluate is worked up to a factor VIII/vWF-complex-preparation.

Surprisingly it has been found in the course of the present invention that the factor VIII/vWF-complex can be provided in high purity and simultaneously in a high yield by means of a cation exchange chromatography, starting from.plasma or a plasma fraction.

As the plasma fraction, e.g. a cryoprecipitate, possibly after a preceding adsorption treatment for removing prothrombin-complex, or a Cohn-fraction is used.

The method is excellently suited for purifying factor VIII-complex from a plasma fraction on an industrial scale, since due to the effective purification, a plurality of further purification steps, e.g. further chromatographic purification steps, are not required. Surprisingly it has been shown that by means of the simple cation exchange chromatography, the factor VIII-complex can be obtained in an at least 300-fold purity as compared to plasma, preferably an at least 400-fold purity, with a simultaneous high yield of at least 50%, preferably at least 60%, based on plasma. Thus, preferably, the purification procedure is to be designed such that only one single chromatographic purification is carried out, i.e. the one on the cation exchanger. Usually this chromatographic purification is carried out as the terminal purification step, before the factor VIII-complex is formulated into a pharmaceutical preparation.

Usually the starting material is applied to the cation exchanger in a calcium-containing buffer. Immediately before application thereof, also a measure for inactivating potentially present viruses, such as human-pathogenic viruses which can be transmitted by blood, is conceivable. For this, a treatment with a virucidal detergent or with an organic solvent and/or detergent is preferred. A treatment with Triton or Tween in the presence of TNBP (tri-(n-butyl)-phosphate) is, e.g., carried out according to EP 0 131 740. By a subsequent cation exchange chromatography the virucidal agent is effectively removed. If the adsorbed complex is washed, such washing preferably is effected with a washing buffer whose ionic strength is above that of the adsorption buffer, e.g. higher by 10–30%. For an elution of the factor VIII/vWF-complex, preferably the ionic strength is further increased. Elution of the factor VIII/vWF-complex is achieved by increasing the ionic strength, which preferably is increased by at least 50%, most preferred by at least 100%, as compared to the ionic strength of the starting solution. The elution buffer preferably contains sodium chloride. To formulate a pharmaceutical factor VIII/vWF-complex-preparation, usually diafiltration and sterile-filtration, as well as optionally a lyophilization, are effected.

The activity of factor VIII or of vWF, respectively, is hardly affected by the cation exchange chromatography. It has proven that the yield of the factor VIII-complex of more than 90%, based on the activity prior to chromatography, is ensured. Therefore, chromatographic purification can be done without common stabilizers of factor VIII, such as, e.g., antithrombin III and/or heparin.

Contrary to methods known in the prior art, in which the cation exchange chromatography has always been contemplated exclusively for already purified factor VIII/vWF-complex-preparations (cf. EP 0 600 480 A2), according to the invention it has been shown that the cation exchange chromatography is excellently suited for a direct purification of factor VIII/vWF-complex from plasma or from a (crude) plasma fraction. With such a method it is not even necessary to provide further chromatographic methods for preparing a factor VIII/vWF-complex-preparation, since the purity which is achieved by the cation exchange chromatography starting from plasma or from a plasma fraction already meets all the demands made on commercially available factor VIII/vWF-complex-preparations.

DETAILED DESCRIPTION

The invention will now be explained in more detail by way of the following examples; however, it shall not be restricted to these exemplary embodiments.

Example 1 describes the purification of plasmatic factor VIII/vWF-complex by cation exchange chromatography and step-wise elution; Example 2 describes the purification of factor VIII/vWF-complex by a combination of anion/cation exchange chromatography and step-wise elution from the cation exchanger; Example 3 describes the purification of rvWF/rfactor VIII-complex by means of cation exchanger; Example 4 describes the isolation of factor VIII/vWF-complex via cation exchange.

EXAMPLE 1

Purification of Plasmatic FVIII-complex by Cation Exchange Chromatography

Cryoprecipiate from human plasma was dissolved in sodium-acetate-buffer, pH 7, and 20 units of heparin per ml solution were added. 0.25 ml of 2% Al(OH)$_3$ suspension were added per 1 g of cryoprecipitate, and incubated for 30 minutes. Subsequently, it was centrifuged at 10 000 rpm for 20 minutes so as to obtain a cryoprecipitate free of turbidity.

A chromatographic column was filled with Fractogel® EMD-SO3 and rinsed with buffer (30 mM glycine-NaCl-buffer). Subsequently, dissolved cryoprecipitate was filtered through the cation exchange column, and such proteins were obtained in the effluent which do not bind to the exchanger (Fraction 1). Unspecifically bound proteins were removed by rinsing the column with 0.3 M NaCl in buffer (Fraction 2). Subsequently, FVIII/vWF-complex was eluted from the exchanger column by elution with 0.4 M and 0.5 M NaCl, respectively (Fraction 3 and Fraction 4, respectively).

From Table 1 it is apparent that both vWF and FVIII are bound by the cation exchanger. By rinsing the cation exchanger column with 0.3 M NaCl (Fraction 2), not any vWF, and only 10% of the FVIII activity were obtained. By this elution step, the FVIII that was not present as a complex with functionally active vWF was separated. By subsequent desorption with 0.4 M NaCl (Fraction 3), FVIII/vWF-complex was obtained which contained approximately 20% of the functionally active vWF and approximately 30% of the total amount of FVIII. Subsequently, the remaining FVIII complex was eluted from the cation exchanger by means of 500 mM NaCl (Fraction 4). Fraction 4 contained factor VIII/vWF-complex containing 80% of the vWF activity and 50% of the FVIII activity, departing from the cryoprecipitate. On account of the cation exchange chromatography, a 20-fold purification of FVIII (specific activity: 12 IU FVIII:C/mg protein) as compared to the cryoprecipitate, and a 350-fold purification of FVIII, based on plasma, was achieved (Fraction 4). From Fraction 3 FVIII can be recovered.

Figure 1:
FIG. 1 shows a vWF multimer analysis of factor VIII/vWF-complex from cryoprecipitate, before and after purification with cation exchanger.

FIG. 1 shows the vWF multimer analysis of factor VIII/vWF-complex before and after purification with cation exchanger, lane A illustrating the vWF multimer pattern of the cryoprecipitate, lane B that of the 300 mM NaCl-eluate (Fraction 2, Table 1), lane C that of the 400 mM NaCl-eluate (Fraction 3, Table 1), and lane D that of the 500 mM eluate (Fraction 4, Table 1). From FIG. 1 it is apparent that by the cation exchange chromatography, a factor VIII/vWF complex with a high-molecular molecular vWF multimer structure is obtained. Factor VIII/vWF-complex containing low-molecular vWF multimers either is not bound to the cation exchanger (Fraction 1) or is separated at the elution with 0.3 M NaCl (Fraction 2).

TABLE 1

Purification of FVIII/vWF-complex from cryoprecipitate by means of cation exchange chromatography

| Sample | vWF:Risto-CoF-activity (U/ml) | FVIII:C activity (U/ml) |
| --- | --- | --- |
| Cryoprecipitate | 2.2 | 2.4 |
| Fraction 1 (Not bound) | 0 | 0 |
| Fraction 2 (Eluate 300 mM NaCl) | 0 | 0.1 |
| Fraction 3 (Eluate 400 mM NaCl) | 1.8 | 3.6 |
| Fraction 4 (Eluate 500 mM NaCl) | 1.8 | 1.5 |

EXAMPLE 2

Purification of Plasmatic FVIII/vWF-complex by a Combination of Anion/Cation Exchange Chromatography Cryoprecipitate of human plasma was dissolved in a buffer of 7 mM Tris, 100 mM Na acetate, 100 mM lysine, 120 mM NaCl, at pH 6.7. Al(OH)$_3$ was stirred in as a pre-treatment. Subsequently, the precipitate was separated by centrifugation.

Cryoprecipitate pre-treated in this manner was applied to a column of Fractogel® EMD-TMAE. Non-bound proteins were obtained by rinsing the column with solution buffer (Fraction 1). This fraction contained 60% of the vWF activity, but merely 10% of the FVIII activity. By eluting the column with 400 mM NaCl (Fraction 2), FVIII/vWF-complex was subsequently obtained. Fraction 2 contained the remaining vWF activity and 70% of the FVIII activity, departing from the cryoprecipitate.

TABLE 2

Purification of FVIII/vWF-complex by a combination of anion and cation exchange chromatography

| Sample | vWF:Risto-CoF-activity (U/ml) | FVIII:C activity (U/ml) |
|---|---|---|
| Cryoprecipitate | 12.5 | 12.2 |
| Fraction 1 (Not bound) | 3.5 | 0.7 |
| Fraction 2 (Eluate 400 mM NaCl) | 2.5 | 14.5 |

The FVIII/vWF-complex of Fraction 2 was diluted 4-fold with 20 mM glycine/NaCl-buffer, and subsequently applied to a cation exchange column of Fractogel® EMD-SO3. Non-binding proteins were obtained in Fraction 1. Weakly bound proteins were removed by rinsing the column with 200 mM NaCl (Fraction 2). Subsequently, it was eluted step-wise with 400 mM NaCl (Fraction 3) and 500 mM NaCl (Fraction 4). In each one of Fractions 3 and 4, 45% of the vWF-activity, and 55% or 40%, respectively, of the FVIII activities were found.

TABLE 3

Purification of FVIII/vWF-complex by a combination of anion and cation exchange chromatography

| Sample | vWF:Risto-CoF-activity (U/ml) | FVIII:C activity (U/ml) |
|---|---|---|
| Starting material | 0.63 | 3.6 |
| Fraction 1 (Not bound) | 0 | 0 |
| Fraction 2 (Eluate 200 mM Nacl) | 0 | 0 |
| Fraction 3 (Eluate 400 mM NaCl) | 0.3 | 2.26 |
| Fraction 4 (Eluate 500 mM NaCl) | 0.25 | 1.43 |

From Table 3 it is apparent that both vWF and FVIII are bound by the cation exchanger. By rinsing the cation exchanger column with 0.2 M NaCl (Fraction 2), not any active vWF and not any FVIII were found. The FVIII/vWF-complex was eluted subsequently in Fractions 3 and 4.

While the specific activity of FVIII:C was 0.59 U/mg protein in the cryoprecipitate, the specific activity of FVIII:C in Fractions 3 and 4 was 500 U/mg protein and 477 U/mg protein, respectively. Departing from cryoprecipitate, the specific activity of vWF rose from 0.6 U/mg protein to 66 U/mg protein and to 83 U/mg protein in Fractions 3 and 4.

Figure 2:
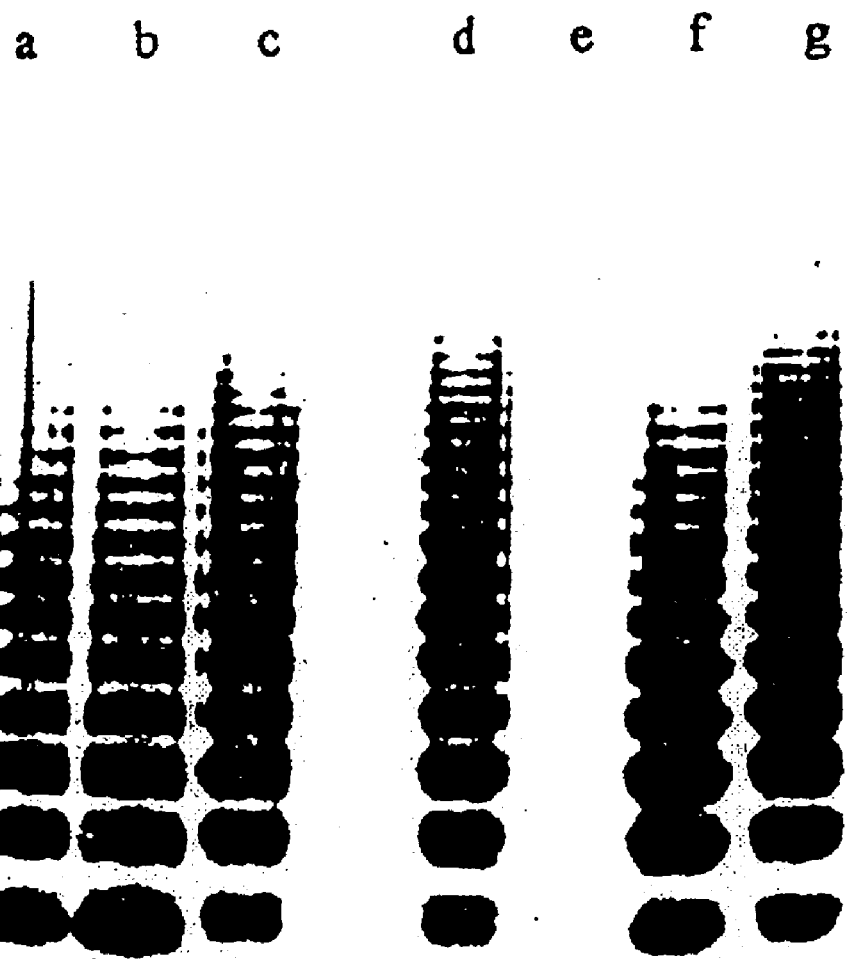
FIG. 2 shows a vWF multimer analysis of factor VIII/vWF-complex from cryoprecipitate, before and after purification by means of a combined anion/cation exchange chromatography.

FIG. 2 shows the vWF multimer analysis of factor VIII/vWF-complex before and after purification with a combined anion/cation exchange chromatography, lanes a to c illustrating the chromatography on the anion exchanger, and lanes d to g those on the cation exchanger. In lane a, FIG. 2 shows the vWF multimer pattern of the cryoprecipitate, in lane b that of the effluent (Fraction 1, Table 2), in lane c that of the 400 mM NaCl eluate (Fraction 2, Table 2), in lane d that of the 400 mM NaCl eluate (Fraction 2, Table 2) before the cation exchanger, in lane e that of the 200 mM NaCl eluate (Fraction 2, Table 3), in lane f that of the 400 mM NaCl eluate (Fraction 3, Table 3), and in lane g that of the 500 mM NaCl eluate (Fraction 4, Table 3).

EXAMPLE 3

Purification of an rvWF/rFVIII-complex by means of cation exchange chromatography (at present considered by applicant to be the best mode of carrying out the invention).

1000 ml of a cell culture supernatant containing recombinant rFVIII/rvWF-complex were applied onto a column filled with 20 ml of Fractogel® TSK-SO3. After having washed the column with buffer, pH 7.4, with 250 mM NaCl, the bound rFVIII/rvWF-complex was eluted by means of a buffer, pH 7.4, with 600 mM NaCl. In Table 4 the results of this column run are illustrated.

TABLE 4

Purification of recombinant rFVIII/rvWF-complex by means of cation exchange chromatography

| Sample | FVIII:C activity (U/ml) | vWF:Risto-CoF activity (U/ml) |
|---|---|---|
| Starting material | 2.3 | 0.1 |
| Effluent | 0.1 | 0 |
| 250 mM NaCl eluate | 0.2 | 0 |
| 600 mM NaCl eluate | 85 | 4.4 |

The example illustrates that a complex comprised of recombinant FVIII and recombinant vWF (which normally is incurred during the fermentation of recombinant FVIII) binds to a cation exchanger and can be eluted selectively, separately from accompanying proteins, by increasing the salt concentration.

In this example a rFVIII/rvWF-complex having a specific FVIII activity of 130 U/mg protein was obtained in a yield of 75%. This corresponds to a purification factor of 28 for this step. The specific activity of rvWF is greatly dependent on the quality of the expressed rvWF. In this instance, it was at 7 U/mg in the eluate, corresponding to a purification factor of 35.

By varying the rFVIII/rvWF-relationship in the starting material, or by following up with a further chromatographic step, the specific activity of FVIII:C may still be further improved.

EXAMPLE 4

Isolation of the Factor VIII/vWF-complex Via Cation Exchange

Example 4A 210 g cryoprecipitate are dissolved in 950 ml $CaCl_2$-heparin-containing citrated buffer and adjusted to pH 6.0.

Insoluble material, mainly fibrinogen, was separated. To inactivate possibly present pathogenic viruses, the clear solution was treated with 1% Triton X100 and 0.3% TNBP (tri-(n-butyl)-phosphate).

100 ml of Fractogel EMD-$SO_3^-$-650 (M) from Merck Darmstadt (DE) were used for adsorption of the virus-inactivated FVIII, which previously had been equilibrated at pH 6.0 in an acetate-buffered NaCl solution having a conductivity of 10 mS/cm.

The FVIII was eluted from the gel by increasing the ionic strength to 500 mM NaCl, washing had previously been carried out with 500 ml 150 mM NaCl solution.

Example 4B

In this Example, Toyopearl SP-550 C was used instead of Fractogel EMD-SO$_3^-$.

|  | Results | | |
|---|---|---|---|
|  | Yield/Plasma | | Purity as compared to |
|  | FVIIIc | FvWF | plasma |
| Example 4A | 62% | 68% | 450 x |
| Example 4B | 56% | 62% | 370 x |

FVIIIc and FvWF were recovered in the same fraction.

What is claimed is:

1. A method of recovering factor VIII/von Willebrand factor-complex (factor VIII/vWF-complex) comprising:
   (a) providing protein solution comprising a factor VIII/vWF complex containing high-molecular weight vWF multimers,
   (b) binding said factor VIII/vWF-complex containing high-molecular weight vWF multimers to a cation exchanger, and
   (c) eluting said cation exchanger by a step-wise elution process to elute and recover said factor VIII/vWF-complex containing high-molecular weight vWF multimers.

2. A method as set forth in claim 1, wherein
said protein solution contains a contaminating protein, said contaminating protein including a factor VIII/wVF complex containing low-molecular weight vWF multimers, factor VIII free from platelet agglutinating vWF activity, or factor VIII:C;
said binding comprising contacting said protein solution with said cation exchanger at a salt concentration of ≦250 mM, whereby said factor VIII/vWF-complex containing high-molecular weight vWF multimers and said contaminating protein become bound to said cation exchanger; and
a step in said step-wise elution process comprises eluting said contaminating protein from said cation exchanger at a salt concentration of between ≧250 mM and ≦300 mM.

3. A method as set forth in claim 1, wherein said eluting step comprises eluting said factor VIII/vWF-complex containing high-molecular weight vWF multimers from said cation exchanger at a salt concentration of ≧300 mM.

4. A method as set forth in claim 1, wherein said eluting step comprises eluting said factor VIII/vWF-complex containing high-molecular weight vWF multimers from said cation exchanger at a salt concentration of ≧350 mM.

5. A method as set forth in claim 3, wherein said recovered factor VIII/vWF-complex is a factor VIII/vWF complex-containing fraction, free from low-molecular vWF multimers, vWF degradation products, non complexed factor VIII, and is substantially free of contaminating nucleic acids.

6. A method as set forth in claim 1, wherein said elution of said factor VIII/vWF complex containing high-molecular weight vWF multimers from said cation exchanger is carried out in a buffer system having a pH ranging between 4.5 and 8.5.

7. A method as set forth in claim 6, wherein said pH of said buffer system is ≧7.1 and ≦8.5.

8. A method as set forth in claim 1, wherein said cation exchanger is sulfopropyl-group conjugated carrier or a carboxymethyl-group conjugated carrier.

9. A method as set forth in claim 1, wherein said protein solution is selected from the group consisting of a plasma, a plasma fraction, a cryoprecipitate, a cell-free supernatant of a recombinant cell culture, an extract of a recombinant cell culture, and a protein fraction enriched in factor VIII/vWF-complex.

10. A method as set forth in claim 2, wherein said eluting step comprises eluting said factor VIII/vWF-complex containing high-molecular weight vWF multimers at a salt concentration of ≧300 mM.

11. A method as set forth in claim 2, wherein said eluting step comprises eluting said factor VIII/vWF-complex containing high-molecular weight vWF multimers at a salt concentration of ≧350 mM.

* * * * *

UNITED STATES PATENT AND TRADEMARK OFFICE
CERTIFICATE OF CORRECTION

| | | |
|---|---|---|
| PATENT NO. | : 6,831,159 B1 | Page 1 of 1 |
| APPLICATION NO. | : 09/367459 | |
| DATED | : December 14, 2004 | |
| INVENTOR(S) | : Arthur Mitterer et al. | |

It is certified that error appears in the above-identified patent and that said Letters Patent is hereby corrected as shown below:

On the title page item (54) and col. 1, line 1, delete "METHOD FOR PURIFYING FACTOR VIII/VWF COMPANY BY CATION-EXCHANGE CHROMATOGRAPHY" and insert therefor -- METHOD OF PURIFYING FACTOR VIII/VWF-COMPLEX BY MEANS OF CATION EXCHANGE CHROMATOGRAPHY--

Signed and Sealed this

Twenty-sixth Day of June, 2007

JON W. DUDAS
*Director of the United States Patent and Trademark Office*